(12) United States Patent
Nairne et al.

(10) Patent No.: US 8,795,631 B2
(45) Date of Patent: Aug. 5, 2014

(54) RADIOFLUORINATION

(75) Inventors: Robert James Domett Nairne, Amersham (GB); Erik Arstad, London (GB); Matthias Eberhard Glaser, London (GB)

(73) Assignees: HammerSmith Imanet Limited, Lonndon (GB); GE Healthcare Limited, Buckinghamshire (GB)

( * ) Notice: Subject to any disclaimer, the term of this patent is extended or adjusted under 35 U.S.C. 154(b) by 104 days.

(21) Appl. No.: 13/119,468

(22) PCT Filed: Oct. 20, 2009

(86) PCT No.: PCT/EP2009/063743
§ 371 (c)(1),
(2), (4) Date: Mar. 17, 2011

(87) PCT Pub. No.: WO2010/060694
PCT Pub. Date: Jun. 3, 2010

(65) Prior Publication Data
US 2011/0189089 A1     Aug. 4, 2011

Related U.S. Application Data

(60) Provisional application No. 61/106,685, filed on Oct. 20, 2008.

(30) Foreign Application Priority Data

Oct. 21, 2008   (GB) .................................. 0819293.2

(51) Int. Cl.
*A61K 51/00* (2006.01)
*A61M 36/14* (2006.01)

(52) U.S. Cl.
USPC ......... 424/1.85; 424/1.89; 422/159; 564/183; 564/489; 546/87

(58) Field of Classification Search
None
See application file for complete search history.

(56) References Cited

U.S. PATENT DOCUMENTS

2008/0274046 A1 *  11/2008  Prenant ........................ 424/1.49

FOREIGN PATENT DOCUMENTS

WO  WO 2004080492 A1 *  9/2004
WO  WO 2007148074 A1 *  12/2007

OTHER PUBLICATIONS

Tewson. Nucl. Med. Biol. 1997, 24, 755-760.*
Saha et al. J. Org. Chem. 2008, 73, 6867-6870.*
Melnyk et al. Biopolymers, 2000, 55, 165-186.*
Lehel et al. J. Labelled Cpd. Radiopharm. 43, 807-815 (2000).*
Gilissen C et al: "Synthesis of N-(2-A18Fufluoroethyl)-N'-Methyltiourea: A Hydrogen Peroxide Scavenger" Journal of Labelled Compounds and Radiopharmaceuticals, John Wiley, Chichester, GB, vol. XLI, Jan. 1, 1998, pp. 491-502.
Glaser M et al: "Click Labeling With 2-[18F]Fluoroethylazide for Positron Emission Tomography" Bioconjugate Chemistry, ACS, Washington, DC, US, vol. 18, Apr. 13, 2007, pp. 989-993.
Hamman S et al: "Selective Reduction of Beta-Fluoroazides to Beta-Fluoroamines" Journal of Fluorine Chemistry, Elsevier, NL, vol. 37, No. 2, Nov. 1, 1987, pp. 191-196.
Bohumil Dolensky et al: "New Building Blocks for Fluorinated Imidazole Derivatives: Preparation of Beta-Fluoro-and Beta, Beta-Difluorohistamine" J. Org. Chem., vol. 66, 2001, pp. 4687-4691.
Kachur et al: "Applied Radiation and Isotopes" 1999, 51, pp. 643-650.
Organic Chemistry Protal, "Reduction of Azides" [Online]. Found At http://www.organic-chemistry.org/systhesis/NIH/reductionsazides.shtm [Accessed Feb. 16, 2009].
PCT/EP2009/063743 ISRWO Dated Feb. 15, 2010.
GB 0819293.2 Search Report Dated Feb. 17, 2009.

* cited by examiner

*Primary Examiner* — Michael G Hartley
*Assistant Examiner* — Sean R Donohue (57) ABSTRACT

The present invention relates to $^{18}$F radio-chemistry and in particular to a method for synthesising radiofluorinated amides and amines. The method of the invention has particular application in the radiosynthesis of a variety of $^{18}$F-labelled positron emission tomography (PET) tracers.

14 Claims, 6 Drawing Sheets

RADIOFLUORINATION

This application is a filing under 35 U.S.C. 371 of international application number PCT/EP2009/063743, filed Oct. 20, 2009, which claims priority to Great Britain application number 0819293.2 filed Oct. 21, 2008 and U.S. application No. 61/106,685 filed Oct. 20, 2008, the entire disclosure of each of which is hereby incorporated by reference.

TECHNICAL FIELD OF THE INVENTION

The present invention relates to $^{18}F$ radiochemistry and in particular to a method for synthesising radiofluorinated amides and radiofluorinated amines. The method of the invention has particular application in the radiosynthesis of a variety of radiofluorinated positron emission tomography (PET) tracers.

DESCRIPTION OF RELATED ART

Fluorine-18 can be considered to be an ideal positron emitter for use in positron emission tomography (PET). It has a half-life of 110 minutes, enabling scans to be conducted over several hours, and has a low positron emission energy which permits images of high resolution. Nucleophilic substitution by fluoride ion is regarded as one of the most attractive ways for introducing fluorine into an organic compound.

Particularly for some large and/or complex molecules, direct nucleophilic radiofluorination with no-carrier-added [$^{18}F$]-fluoride, or with simple $^{18}F$-labelled electrophilic precursors can be difficult. The strategy that has been commonly used to overcome this issue is to first introduce $^{18}F$ onto a precursor, which is in turn used to carry out a nucleophilic substitution reaction. The types of prosthetic groups used for this type of radiofluorination include $^{18}F$-labelled alkylating agents, $^{18}F$-labelled acylating agents, and $^{18}F$-labelled fluoroaryl precursors (see for example pages 258-261 of "Handbook of Radiopharmaceuticals: Radiochemistry and Applications" 2003; Wiley: Welch and Redvanly, Eds.). This approach to $^{18}F$-labelling of compounds is also attractive as it avoids the need for optimisation of radiochemistry for each compound.

Alkyl amides are known to be good precursors for $^{18}F$-labelling. However, direct labeling of these materials can result in cyclisation of the alkyl tosylate onto the carbonyl of the amide group rather than the desired fluoroalkyl amide, as illustrated in the scheme below:

wherein OTs represents tosylate and R represents a hydrocarbon substituent.

Gilssen et al (J. Labelled Comp. Radiopharm. 1998; XLI: 491-502) reported two different methods for the preparation of [$^{18}F$]-fluoroethyl amine. One method was from an N-Tert-butyloxycarbonyl (N-BOC)-protected starting compound, having a radiochemical yield of 1%. The second method was from an N-phthalimide-protected starting group, having a radiochemical yield of 30%. While the second method is clearly superior, there is still scope for further improvement of the radiochemical yield.

Jelinski et al (J. Labelled Comp. Radiopharm. 2002; 45: 217-29) reported the preparation of [$^{18}F$]-fluoroethyl amine using N-BOCaminoethyl tosylate as the starting compound:

However, the radiochemistry has been found by the present inventors to be poor. Several reactions carried out by the present inventors using different solvents, including acetonitrile methanol and DMSO, failed to give more than a 3% isolated yield of the desired [$^{18}F$]fluoroethylamine.

There is therefore a need to improve the synthesis of radiofluorination precursors useful in the radiosynthesis of $^{18}F$-labelled amides and $^{18}F$-labelled amines.

SUMMARY OF THE INVENTION

The method of the present invention makes use of the reduction of azides to amines to facilitate the production of a range of radiofluorinated amide and amine compounds. The present inventors have found that the methods of the invention have superior radiochemistry in comparison to the prior art methods. In certain aspects, the methods of the invention permit more facile automation than possible with the prior art methods.

DETAILED DESCRIPTION OF THE INVENTION

In one aspect, the present invention provides a radiofluorination method comprising:

(i) radiofluorination of an azide of Formula Ia with a suitable source of [$^{18}$F]-fluoride ion to obtain a radiofluorinated azide of Formula Ib:

$$N_3-R^1-LG \xrightarrow{^{18}F^-} N_3-R^1-^{18}F$$
$$\text{(Ia)} \qquad\qquad\qquad \text{(Ib)}$$

wherein said radiofluorination is carried out in a solvent suitable for said radiofluorination, and wherein;
$R^1$ is $C_{1-10}$ alkylene, $C_{3-10}$ cycloalkylene, $C_{4-20}$ cycloalkylene-alkylene, $C_{5-14}$ arylene, $C_{6-20}$ alkylene-arylene, $C_{1-10}$ hetero alkylene, $C_{2-10}$ heterocycloalkylene, $C_{3-13}$ heteroarylene, $C_{6-20}$ heteroalkylene-arylene, $C_{6-20}$ alkylene-heteroarylene, or $C_{6-20}$ heteroalkylene-heteroarylene, wherein $R^1$ has between 0-3 substituents selected from $C_{1-4}$ alkyl, $C_{5-10}$ aryl, amino, hydroxy, halo or nitro; and, wherein $R^1$ optionally comprises one or more protecting groups;
and LG is a suitable leaving group;
(ii) reduction of the radiofluorinated azide of Formula Ib to obtain a radiofluorinated amine of Formula Ic:

$$H_2N-R^1-^{18}F \qquad\qquad \text{(Ic)}$$

wherein said reduction is carried out in a solvent suitable for said reduction; and
wherein $R^1$ is as defined in step (i).

In the radiofluorination method of the present invention, the term "suitable source of [$^{18}$F]-fluoride ion" means [$^{18}$F]-fluoride ion in a form which can displace LG of Formula Ia in order to obtain a [$^{18}$F]-fluorine-labelled (also termed "radiofluorinated") compound.

A "solvent suitable for said radiofluorination" suitably comprises an organic solvent. The term "organic solvent" is used to refer to a non-aqueous carbon-based solvent.

The term "alkylene", used either alone or in combination, refers to a straight or branched chain or cyclic divalent hydrocarbon radical having a specified number of carbon atoms. Alkylene groups include those with 1-10 carbon atoms. Examples of alkylenes as used herein include, but are not limited to, methylene, ethylene, propylene, butylene and the like.

For the term "cycloalkylene", used either alone or in combination, at least 3 carbons must be present. Such cyclic moieties include cyclopropylene, cyclobutylene, cyclopentylene, cyclohexylene and cycloheptylene.

The term "cycloalkylene-alkylene" refers to a cycloalkylene moiety as defined above bonded to an alkylene moiety as defined above.

The term "arylene", used either alone or in combination, refers to divalent unsaturated aromatic carboxylic radicals having a single ring, such as phenylene, or multiple condensed rings, such as naphthylene or anthrylene. Arylene groups include those with 5-14 carbon atoms. Examples of arylenes as used herein include, but are not limited to, benzene-1,2-diyl, benzene-1,3-diyl, benzene-1,4-diyl, naphthalene-1,8-diyl, and the like.

The term "alkylene-arylene" refers to an alkylene moiety as defined above bonded to an arylene moiety as defined above.

The terms "heteroalkylene", "heterocycloalkylene" and "heteroarylene", used herein either alone or in combination, are, respectively, an alkylene, cycloalkylene and arylene, as defined above, wherein at least one atom in the chain or ring is a heteroatom selected from N, S or O.

The term "heteroalkylene-arylene" refers to a heteroalkylene iety as defined above bonded to an arylene moiety as defined above.

The term "alkylene-heteroarylene" refers to an alkylene moiety as defined above, bonded to a heteroarylene moiety as defined above.

The term "heteroalkylene-heteroarylene" refers to a heteroalkylene moiety as defined above bonded to a heteroarylene moiety as defined above.

"Alkyl" used either alone or as part of another group is defined herein as any straight, or branched saturated or unsaturated $C_nH_{2n+1}$ group, wherein unless otherwise specified n is an integer between 1 and 10. Alkyl groups include for example methyl, ethyl, propyl, isopropyl, butyl, isobutyl, t-butyl, 1-methylpropyl, pentyl, isopentyl, sec-pentyl, hexyl, heptyl, and octyl.

"Aryl" is defined herein as any mono-, bi- or hi-cyclic $C_{5-14}$ molecular fragment or group comprising at least one aromatic ring, and preferably having 5 to 6 ring members in each ring. The term aryl embraces purely aromatic radicals such as phenyl, naphthyl, tetrahydronaphthyl, indane, and biphenyl, as well as radicals comprising at least one aromatic ring fused with one or more cycloalkyl or heterocycloalkyl rings.

The term "amino" means an —NH$_2$ group.
The term "hydroxyl" means an —OH group.
The term "nitro" means an —NO$_2$ group.
The term "halo" means a halogen substituent selected from fluorine, chlorine, bromine, and iodine.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl, benzyl; acetyl; benzoyl; trityl (Trt) or trialkylsilyl such as tetrabutyldimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999).

A "leaving group" (LG) is an atom or a group of atoms that is displaced by [$^{18}$F]-fluoride taking with it the bonding electrons.

The choice of "solvent suitable for said reduction" depends on the reducing agent used. Various suitable methods of reduction are discussed in more detail below. For example, an anhydrous aprotic solvent such as tetrahydrofuran (THF) would be suitable where lithium aluminium hydride is the reducing agent. The term "aprotic solvent" is organic solvent that does not exchange protons with a substance dissolved in it, examples include acetone and dichloromethane. On the other hand, protic solvents are suitable where sodium borohydride is the reducing agent. The term "protic solvent" means a solvent containing or able to release protons and/or able to form hydrogen bonds. Examples of protic solvents are water and alcohols, e.g. $C_{1-6}$ alkanols (preferably methanol, ethanol, n-propanol, iso-propanol, n-butanol, sec-butanol, tert-butanol), and mixtures of two or more of these solvents. Suitable mixing ratios can readily be determined by one of ordinary skill in the art.

Methods for obtaining a broad range of azide compounds are well known in the art. For example, azides can be prepared by aliphatic nucleophilic substitution. The appropriate alkane bearing a leaving group is treated with azide ion. The leaving group can be a halide (Marti et al Tetrahedron Lett 1989; 30: 1245), hydroxy (Viaud and Rollin Synthesis 1990; 130), mesylate or tosylate (Screiven and Turnbull 1988 Chem. Rev; 88: 306) and acetoxy (Murahashi et al Org. Chem. 1989; 54:3292). A facile way to obtain the azide of Formula Ia, which further comprises LG, is to include two leaving groups in the starting compound, one of which remains following nucleophilic substitution.

In a method described by van Velzen et al (Synthesis 1995; 989-997), 2-fluoroethyl tosylate was prepared from 2-fluoroethanol, pyridine, and tosyl chloride in $CH_2Cl_2$ at room temperature for 2.5 h. By addition of sodium azide, an azide of Formula Ia wherein $R^1$ is ethylene is obtained, i.e. 2-fluoroethyl azide. This method may be adapted to obtain a number of other azides of Formula Ia.

Alternatively, azides can be obtained by treatment of monosubstituted hydrazines with nitrous acid in a reaction analogous to the formation of aliphatic diazo compounds (Patai "The Chemistry of Diazonium and Diazo Groups"; Wiley: NY, 1978, articles by Hegarty p 511, and Schank p 645).

To carry out the radiofluorination step (i) of the method of the present invention, various well-known strategies can be used to ensure optimal reactivity of [$^{18}$F]-fluoride ion.

First of all, in order to increase the reactivity of [$^{18}$F]-fluoride ion, and to avoid hydrolysis, water is removed from fluoride prior to the reaction and the radiofluorination reactions are typically carried out wherein the solvent is anhydrous (Aigbirhio et al 1995 J. Fluor. Chem.; 70: 279-87). This removal of water from the fluoride ion is referred to as making "naked" fluoride ion, and is regarded as a step necessary to increase the reactivity of fluoride as well as to avoid hydroxylated by-products resulting from the presence of water (Moughamir et al 1998 Tetr. Lett.; 39: 7305-6). There is some evidence that fluoridations can be carried out without this drying step (WO 2005/097713). Nevertheless, for the present invention, an anhydrous reaction solvent is a preferred solvent for the radiofluorination step (i).

A further step that is used to improve the reactivity of [$^{18}$F]-fluoride ion for radiofluorination reactions is to add a cationic counterion prior to the removal of water. The counterion should possess sufficient solubility within the anhydrous reaction solvent to maintain the solubility of the fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™ because of its good solubility in organic or dipolar aprotic solvents and enhanced fluoride reactivity.

A "dipolar aprotic solvent" is an organic solvent as defined above with characteristically high polarity and low reactivity, i.e., a solvent having a sizable permanent dipole moment that cannot donate labile hydrogen atoms to form strong hydrogen bonds. Non-limiting examples of dipolar aprotic solvents include acetonitrile, dimethyl formamide, dimethyl acetamide, dimethyl sulfoxides, and hexamethylphosphoramide.

Labeling with $^{18}$F in step (i) of the present invention is achieved by nucleophilic displacement of LG from a compound of Formula Ia. Examples of preferred leaving groups LG include Cl, Br, I, tosylate (OTs), nosylate (ONs), brosylate (OBs), mesylate (OMs), and triflate (OTf), preferably OTs, OMs and OTf. An especially preferred leaving group is OTs.

In a preferred embodiment, step (i) of the method of the invention is illustrated in the scheme below, wherein $R^1$ is as suitably and preferably defined herein:

This reaction wherein $R^1$ is ethylene is described by Glaser and Årstad (Bioconjugate Chem 2007; 18: 989-993).

When $R^1$ comprises an aromatic ring, $R^1$-LG may comprise an aromatic ring activated towards nucleophilic fluorination, e.g. aryl iodonium salt, aryl diazonium, aryl trialkylammonium salts or nitroaryl derivatives. Radiofluorination of iodonium salts is reported by Pike et al (J. Chem. Soc. Chem. Comm. 1995: 2215-16), Shah et al (J Chem Soc (Perkin Trans. 1 1998: 2043-6; Martín-Santamaría et al Chem. Comm. 2000: 649-50), Wüst et al (J. Labelled Cpd. Radiopharm. 2001, 44: S12-3). WO 2005/061415 reports that the inclusion of a free radical trap in the reaction mixture improves the reproducibility of these reactions.

The reduction step (ii) of the method of the invention may be:
(a) carried out using a reducing agent;
(b) carried out by electrochemical reduction;
(c) carried out using a phosphine followed by hydrolysis; or,
(d) catalysed by elemental copper in the presence of an acid.

The term "reducing agent" means a chemical compound used to reduce another chemical compound by donating electrons, thereby becoming oxidized. Well-known reducing agents include lithium aluminum hydride, palladium on carbon with cyclohexene or formic acid, nascent hydrogen, sodium amalgam, sodium borohydride, sodium cyanoborohydride, stannous ion, sulfite compounds, hydrazine, zinc-mercury amalgam, diisobutylaluminum hydride, Lindlar catalyst (with a hydrogen source), and oxalic acid. For the reduction of azides to amines, it is commonly known to use lithium aluminum hydride, although this reagent is known to have handling problems associated with its reactivity.

Suitable temperatures for carrying out reduction using a reducing agent can be from room temperature to 120° C.

Electrochemistry is the combination of a heterogenous electron transfer at an electrode with a chemical reaction, and may be used in organic synthesis. For an electrochemical reaction to take place, the substrate diffuses to an electrode where an electron transfer forms a reactive intermediate, which reacts with a low activation energy to form the product. The electrochemical reduction of nitro compounds is reviewed Chapter 9 of "Organic Electrochemistry", Lund and Hamerich, Eds. Electrochemical reduction of an azide to amine and dinitrogen can be achieved in a protic solvent (see page 403 of "Organic Electrochemistry").

An alternative widely-known method for carrying out the reduction step of the method of the invention is by reaction with a phosphine, followed by hydrolysis, otherwise known as the Staudinger reaction (Staudinger and Meyer 1919 Helv. Chim. Acta; 2: 635). An aqueous solvent system is used for this chemistry. The term "aqueous solvent system" refers to a solution where the solvent is water. One downside of the Staudinger reaction is that the phosphine oxide side product is often difficult to remove from the crude product mixture, and from an industrial point of view the use of phosphines is costly, and represents an environmental issue. Furthermore, in the context of radiochemistry, the sequential nature of the Staudinger reaction can make automation difficult.

In a preferred embodiment reduction method (d) is used, i.e. catalysed by elemental copper in the presence of an acid. It has been reported that 2-[$^{18}$F]fluoroethylazide decomposed to $^{18}$F-fluoride at room temperature in the presence of copper and dilute 5% v/v trifluoroacetic acid (TFA) (Glaser & Årstad Bioconjugate Chem 2007; 18: 989-993). Subsequent investigation of the reaction by the present inventors confirmed that it led to clean formation of 2-[$^{18}$F]fluoroethylamine (Example 4), and also that the reaction could be applied for obtaining an aromatic amine from an aromatic azide (Example 5).

TFA is one preferred acid for use in this reduction method, but alternative preferred acids are also possible. In Example 1 below it is shown that excellent yields of the amine were obtained where the acid used was phosphoric acid ($H_3PO_4$), sulphuric acid ($H_2SO_4$), or methane sulfonic acid ($CH_3SO_3H$). $H_3PO_4$, $H_2SO_4$ or $CH_3SO_3H$ are therefore alternative preferred acids for reduction method (d).

In each of the experimental examples below where reduction is catalysed by copper in the presence of an acid, the reduction is carried out at an elevated temperature, i.e. greater than room temperature. In a preferred embodiment, reduction method (d) is carried out at a temperature in the range 60-80° C., most preferably at 60° C.

Method (d) for azide reduction is more straightforward and less harsh than previous methods. This method for reduction therefore provides a superior approach in terms of ease of handling, reduced cost, and facile automation.

The elemental copper may be present in the form of powder, turnings, wire, or nano particles, preferably copper wire or copper powder. Alternatively, elemental copper is formed by reduction of ionic copper to its elemental form by inclusion of a reducing agent in the reaction. Preferred reducing agents for this purpose are sodium ascorbate and ascorbic acid.

Preferably for the method of the invention, $R^1$ is chosen from $C_{1-6}$ alkylene, $C_{1-6}$ heteroalkylene, $C_{3-10}$ cycloalkylene, $C_{5-14}$ arylene, and $C_{3-13}$ heteroarylene, most preferably $C_{1-6}$ alkylene and $C_{5-14}$ arylene, and most especially preferably $C_{1-3}$ alkylene, in particular ethylene. It is preferred that there are no substituents on $R^1$.

In a preferred embodiment of the present invention, the radiofluorination method further comprises:
(iii) reaction of the radiofluorinated amine of Formula Ic with a compound of Formula Id:

(Id)

wherein.
$R^2$ is an R* group selected from $C_{1-10}$ alkyl, $C_{1-10}$ heteroalkyl, $C_{3-10}$ cycloalkyl, $C_{4-20}$ cycloalkyl-alkyl, $C_{5-14}$ aryl, $C_{3-13}$ heteroaryl, $C_{6-20}$ alkylene-aryl, $C_{6-20}$ heteroalkylene-aryl, $C_{6-20}$ alkylene-heteroaryl, $C_{6-20}$ heteroalkylene-heteroaryl, wherein R* is optionally substituted with one or more substituents selected from halo, amino, hydroxy, or nitro; or, $R^2$ is a biomolecule, or a nanoparticle; and, wherein $R^2$ optionally comprises one or more protecting groups; and,
$R^3$ is a suitable activating group (AG), to give a radiofluorinated amide of Formula IIa:

(IIa)

wherein $R^1$ is as defined for steps (i) and (ii) above, and $R^2$ is as defined for Formula Id;
or;
$R^3$ is an R* group, to give a radiofluorinated amine of Formula IIb:

(IIb)

wherein $R^1$ is as defined for steps (i) and (ii) above, and $R^2$ is as defined for Formula Id;
and wherein said reaction step (iii) is carried out in a solvent suitable for said reaction step.

The terms "alkyl", "aryl" "amino", "hydroxyl", "halo", "nitro" and "protecting group" are as previously defined.

The term "heteroalkyl" as defined herein is an alkyl radical as defined above, wherein at least one atom in the chain is a heteroatom selected from N, S or O.

The term "cycloalkyl" is any cyclic alkyl wherein n of $C_nH_{2n+1}$, unless otherwise specified, is an integer between 3 and 10. Examples of cycloalkyl groups include cyclopropyl, cyclobutyl, cyclopentyl, and cyclohexyl.

The term "cycloalkylene-alkyl" refers to a cycloalkylene as defined above conjugated to an alkyl as defined above.

The term "heteroaryl" is an aryl as defined above containing at least one N, O or S atom ring member. Examples of heteroaryl groups include pyrrolyl, pyridinyl, pyridyloxy, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzothiophenyl, benzimidazoyl, quinolinyl, and tetraazolyl.

The term "biomolecule" as used herein means a component or product of a cell such as a peptide, protein, antibody, carbohydrate, lipid, or nucleic acid. Preferred biomolecules are peptides, proteins and antibodies.

A "nanoparticle" is a particle that has a primary particle size (diameter), which is in the order of magnitude of nanometers. That is, nanoparticles have a particle size ranging from about 1 to about 750 nanometers. Nanoparticles with particle sizes ranging from about 2 nm to about 750 nm can be economically produced. Non-limiting examples of particle size distributions of the nanoparticles are those that fall within the range from about 2 nm to less than about 750 nm, alternatively from about 2 nm to less than about 200 nm, and alternatively from about 2 nm to less than about 150 nm. Preferably, nanoparticles suitable for the method of the present invention are made from derivatives of norbornene for ring opening metathesis polymerization (ROMP), protein shells of bacteriophages, or protein coated paramagnetic particles (e.g. $MnFe_2O_4$).

An "activating group" (AG) is an $R^3$ group that results in the compound of Formula Id being an activated carboxylic acid. An "activated carboxylic acid" is derivative of a carboxyl group that is more susceptible to nucleophilic attack than a free carboxyl group.

In this embodiment of the invention, the radiofluorinated amine of Formula Ic is used as a synthon. A "synthon" in the context of the present invention comprises an $^{18}F$-containing structural unit of the desired amide of Formula IIa or amine of Formula IIb. Reaction of said synthon with the direct radiolabelling precursor compound of Formula Id results in said desired amide of Formula IIa or amine of Formula IIb according to the method of the invention.

For step (iii) of the method of the invention, $R^2$ is preferably an $R^*$ group, such that the product is a radiofluorinated small molecule. Preferred $R^*$ groups are $C_{1-10}$ alkyl, $C_{1-10}$ heteroalkyl, $C_{3-10}$ cycloalkyl, $C_{4-20}$ cycloalkyl-alkyl, $C_{5-14}$ aryl, $C_{3-13}$ heteroaryl, $C_{6-20}$ alkylene-aryl, $C_{6-20}$ heteroalkylene-aryl, $C_{6-20}$ alkylene-heteroaryl, and $C_{6-20}$ heteroalkylene-heteroaryl. Preferred substituents for $R^2$ are amino, hydroxy and nitro.

In step (iii), when $R^3$ of Formula Id is an activating group, AG, reaction with the radiofluorinated amine of Formula Ic enables numerous $^{18}F$-labelled amide compounds of Formula IIa to be synthesised. Preferably, step (iii) where $R^3$ is AG is carried out wherein the solvent is a dipolar aprotic solvent, as defined above, in the presence of a base. Examples of suitable bases that can be used are triethylamine and diisopropylamine. As an alternative, a buffer pH 7-9 may be used in place of the base. The reaction may be carried out at temperatures of 25-100° C.

Reaction of an amine with a carboxylic acid or with a carboxylic acid derivative to form an amide is a well-known reaction, especially in the synthesis of biomolecules such as peptides (see for example Barany and Merrifield "Solid Phase Peptide Synthesis" in "The Peptides" Gross and Meienhofer, Eds., Academic Press, New York, 1979, vol. 2, p. 100). To avoid obtaining a salt of the organic acid and base on the simple addition of an amine to a carboxylic acid, the carboxylic acid first needs to be activated. This is achived by treatment of the corresponding carboxylic acid with inorganic acid halides such as $SOCl_2$ or thionyl chloride (see Ansell in Patai "The Chemistry of Acyl Halides"; Wiley NY, 1972, p 35), or with an active ester (Itoh et al 1975 Synthesis; 456-457; and Itoh et al 1974 Tet. Lett., 15(35): 3089-3092). A preferred AG in the amide formation step is an active ester group or equivalent. An "active ester" is an ester made with an alcohol whose structure allows it to be easily displaced by nucleophiles such as amines, forming a stable linkage. An "equivalent" to an activated ester is a group which is not itself an activated ester, but can act as a precursor to an amide in the same way. For example, thiophenyl esters are thioesters rather than esters and are therefore equivalent. In a preferred embodiment, the activating group is selected from N-hydroxysuccinimidyl, N-hydroxyazobenzotriazolyl, pentafluorophenyl, and thiophenyl.

The method of the invention may alternatively be used for the radiosynthesis of radiofluorinated amine compounds by reductive amination. In this embodiment, in step (iii), each of $R^2$ and $R^3$ is an $R^*$ group, as suitably and preferably defined above, such that the compound of Formula Id is an aldehyde or a ketone. A wide range of such aldehydes and ketones are commercially available.

The solvent for carrying out the reductive amination can be organic or aqueous, as defined above. Typically sodium borohydride in methanol or ethanol is used, but any protic solvent as defined above, including water, can work. The amination reaction is preferably carried out at temperatures of between 25-80° C.

To be suitable for mammalian administration, the radiofluorinated amide of Formula IIa, or the radiofluorinated amine of IIb, is formulated as a pharmaceutical composition. A "pharmaceutical composition" is defined in the present invention as a formulation comprising a radiofluorinated amide of Formula IIa, or a radiofluorinated amine of Formula IIb, as suitably and preferably defined herein, or a salt thereof, together with a biocompatible carrier, in a form suitable for administration to humans.

The "biocompatible carrier" is a fluid, especially a liquid, in which the either the radiofluorinated amide or radiofluorinated amine as defined herein is suspended or dissolved, such that the pharmaceutical composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other nonionic polyol materials (e.g. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

The pharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid).

The method of the invention may further include, in any order, one or more of the following steps:
(iv) when any of $R^{1-3}$ comprises one or more protecting groups, removal of said protecting groups; and/or,
(v) removal of excess [$^{18}F$]-fluoride ion, for example by ion-exchange chromatography, and/or,
(vi) where said suitable solvent is an organic solvent, removal of said solvent; and/or,
(vii) formulation of said radiofluorinated amide of Formula IIa or said radiofluorinated amine of Formula IIb together with a biocompatible carrier; and/or
(viii) sterilisation of the formulation of step (vii).

Preferably, the radiofluorinated amide of Formula IIa or radiofluorinated amine of Formula IIb obtained by the method of the present invention is a "PET tracer", i.e. suitable for the detection by positron emission tomography (PET) imaging of a particular biological target within a mammalian subject in vivo. Most preferably, said PET tracer is formulated as a pharmaceutical composition, the suitable and preferred aspects of which are as described above.

Non-limiting examples of particular radiofluorinated PET tracers that can be obtained using the method of the invention include:
1. $^{18}$F-fluoroetanidazole (FETA, for imaging hypoxia; T. J. Tewson, *Nucl. Med. Biol.* 24, 1997, 755-760);
2. (S)-[$^{18}$F]fluoroethylcarazolol (β-adrenoceptor; P. H. Elsing a et al. *J. Lab. Cpd. Radiopharm.* 1999, S372-4);
3. $^{18}$F-forskolin (adenylyl cyclase, D. O. Kiesewetter et al., *J. Fluorine Chem.* 101, 2000, 297-304);
4. $^{18}$F-FNECA (adenosine agonist, S. Lehel et al., *J. Lab. Cpd. Radiopharm.* 43, 2000, 807-815); and,
5. Gly-(2-[$^{18}$F]fluoroethyl)NH[9])-oxytocin (M. Jelinski et al., *J. Lab. Cpd. Radiopharm.* 45, 2002, 217-229)

In a preferred aspect, the method of the invention is automated. Radiofluorinated PET radiotracers are now often conveniently prepared on an automated radiosynthesis apparatus. There are several commercially-available examples of such apparatus, including Tracerlab MX (GE Healthcare) and Tracerlab FX (GE Healthcare). In a preferred embodiment, when the method of the invention is automated, the reduction step is catalysed by elemental copper in the presence of an acid, wherein the elemental copper and acid are as suitably and preferably defined herein. In this way, the automated method is relatively mild and does not suffer from any of the problems related to using the Staudinger reaction. Furthermore, as only dilute acid is required, addition of a nucleophile in the presence of a base allows direct one-pot functionalisation of the amine. This furthermore facilitates automation of the method of the invention by reducing the number of vials required for the method to be carried out.

The reactants for the methods of the invention as described herein may be provided in a kit. Therefore, in another aspect, the present invention further provides a kit for carrying out the method of the invention, said cassette comprising:
(i) a first vessel comprising the azide of Formula Ia as suitably and preferably defined herein; and,
(ii) a second vessel comprising the reagents required for the reduction step (ii) of the method of the invention as suitably and preferably defined herein.

The kit may optionally further comprise:
(iii) means for fluorinating with a suitable source of [$^{18}$F]-fluoride ion, wherein said suitable source of [$^{18}$F]-fluoride is as suitably and preferably defined herein; and optionally,
(iv) a column for the removal of unwanted [$^{18}$F]-fluoride ion.

When the method of the invention is carried out on an automated synthesis apparatus, a "cassette", often disposable, in which the radiochemistry is performed, is fitted to the apparatus. The cassette normally includes fluid pathways, a reaction vessel, and ports for receiving reagent vials as well as any solid-phase extraction cartridges used in the post-radiosynthetic clean up steps. In a further aspect of the invention, a cassette is provided for carrying out the automated method of the invention, wherein said cassette comprises the components as suitably and preferably defined above for the kit of the invention.

The invention is now illustrated by the following non-limiting examples:

BRIEF DESCRIPTION OF THE EXAMPLES

Example 1 describes the preferred reduction step of the method of the invention wherein 2-[$^{18}$F]fluoroethylazide is reduced to 2-[$^{18}$F]fluoroethylamine in the presence of elemental copper and various different acids.

Example 2 describes a two-pot preparation of 9H-beta-carboline-3-carboxylic acid (2-[$^{18}$F]fluoro-ethyl)-amide and its subsequent formulation.

Example 3 describes a one-pot preparation of 9H-beta-carboline-3-carboxylic acid (2-[$^{18}$F]fluoro-ethyl)-amide.

Example 4 describes the synthesis of 2-[$^{18}$F]N-fluoroethyl benzamide.

Example 5 describes the non-radioactive synthesis of benzylamine according to step (ii) of the present invention using copper catalysis, demonstrating that aromatic amines of Formula Ic can also be obtained by the methods described herein.

List of Abbreviations Used in the Examples
° C. degrees Celsius
λ wavelength
μCi microCurie
μl microliter
μm micrometer
Bz benzyl
DMF dimethylformamide
HPLC high performance liquid chromatography
mg milligram
ml milliliter
mm millimeter
min minutes
nm nanometres
PTFE polytetrafluoroethylene (Teflon)
s seconds
TFA trifluoroacetic acid
$t_R$ retention time

EXAMPLES

Example 1

Preparation of 2-[$^{18}$F]Fluoroethylamine

To a conical glass vial (Wheaton, 2 ml) were added a plug of copper wire (0.1 mm, 90-110 mg), acid (100 μl, 20% in water), and 2-[$^{18}$F]fluoroethylazide (100 μl, 279-313 μCi, prepared as described in M. Glaser and E. Årstad, Bioconj. Chem. 2007; 18: 989). The vial was heated at 80° C. for 30 min and an aliquot analyzed by HPLC (column LunaC18, 50×4.6 mm, 3 μm, solvent A: water (0.1% TFA), solvent B: acetonitrile (0.1% TFA), flow 1 ml/min, gradient 5 to 80% solvent B in 15 min, λ=254 nm). The product peak eluted with the solvent front ($t_R$=45 s).

2-[$^{18}$F]Fluoroethylamine was prepared in good yields from 2-[$^{18}$F]fluoroethylazide/copper(0) when the acid used was 10% phosphoric acid, 10% sulfuric acid or 10% methane sulfonic acid. In comparison, when the acid was hydrochloric acid, the yield was relatively low (Table 1).

TABLE 1

Radiochemical yields of 2-[$^{18}$F]fluoroethylamine using alternative acids in the Cu(0) reduction method with 2-[$^{18}$F]fluoroethylazide.

| Experiment | Acid* | Analytical yield of 2-[$^{18}$F]fluoroethylamine |
|---|---|---|
| 1 | HCl | 12% |
| 2 | $H_3PO_4$ | 97% |
| 3 | $H_2SO_4$ | 98% |
| 4 | $CH_3SO_3H$ | 94% |

*total concentration 10%

Example 2

Figure 1:
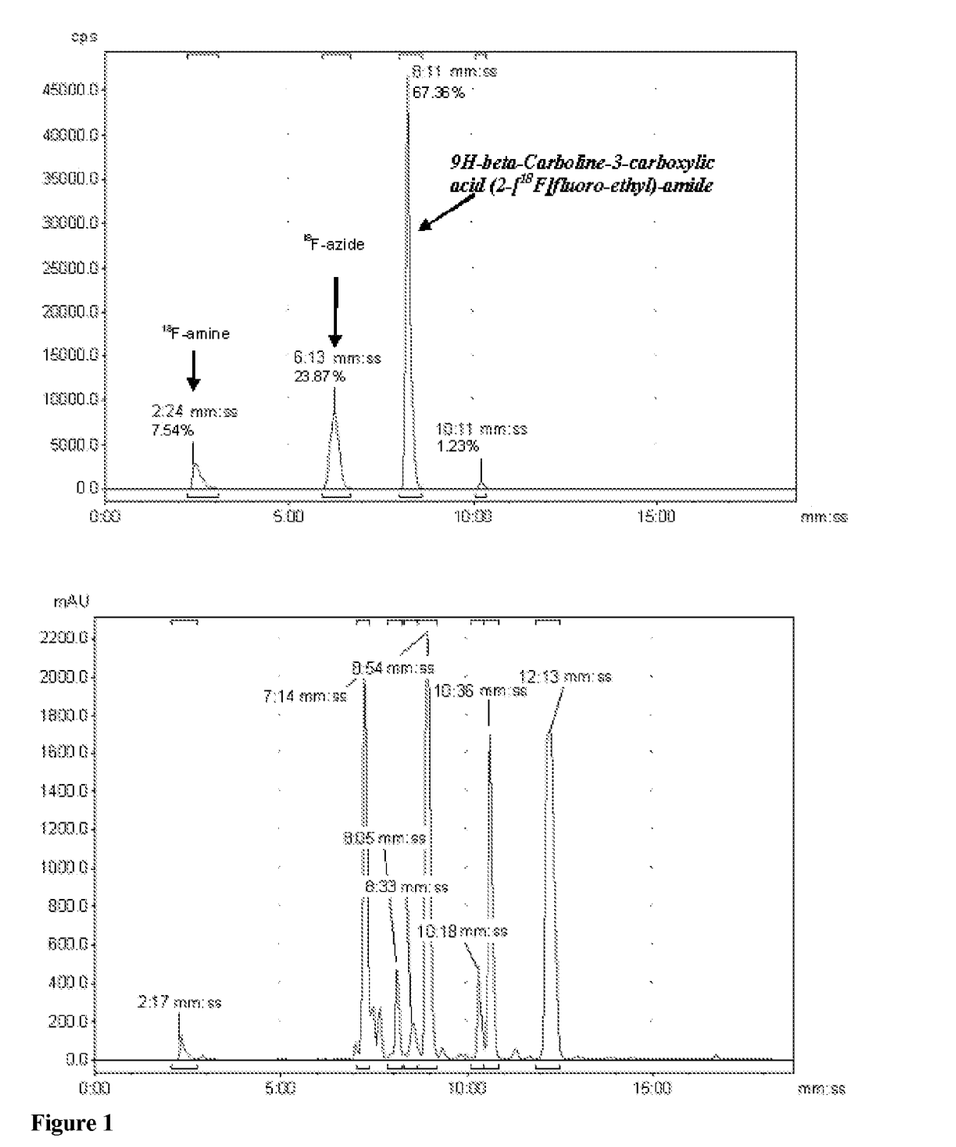
FIG. 1 shows the preparative HPLC chromatogram of 9H-beta-Carboline-3-carboxylic acid (2-[$^{18}F$]fluoro-ethyl)-amide (top: radioactivity channel, bottom: UV channel, 254 nm).

Two-pot Preparation of 9H-beta-carboline-3-carboxylic acid (2-[$^{18}$F]fluoroethyl)amide and Subsequent Formulation 2-[$^{18}$F]fluoroethylazide (17 mCi, prepared as described in M. Glaser and E. Årstad, Bioconj. Chem. 2007; 18: 989-993) in acetonitrile (35 μl) was added to a conical vial containing a plug of copper wire (0.1 mm, 114 mg), followed by a solution of TFA in water (10%, 45 μmol, 35 μl). After heating for 30 min at 80° C., more acetonitrile (50 μl) was added and the reaction solution transferred into another vial. Triethylamine (27 μl, 227 μmol) was added followed by a solution of 9H-beta-Carboline-3-carboxylic acid pentafluorophenyl ester (4 mg, 10.6 μmol; prepared by esterification of the corresponding carboxylic acid, which was obtained by the methods described in EP0030254) in DMF (50 μl). The mixture was heated for 15 min at 80° C. and filtered (Eppendorf pipette tip with plug of tissue). The filter was rinsed with additional acetonitrile (100 μl). HPLC mobile phase (150 μl) was added to the combined filtrate. Purification of the crude reaction mixture was done by preparative HPLC (column Phenomenex Onyx, 100×10 mm, solvent A. water (0.1% TFA), solvent B: acetonitrile (0.1% TFA), flow rate 3 ml/min, gradient 5 to 80% solvent B in 15 min, λ=254 nm). The isolated and decay-corrected radiochemical yield of title compound was 16% (referring to starting 2-[$^{18}$F]fluoroethylazide). FIG. 1 shows the preparative HPLC chromatogram of 9H-beta-Carboline-3-carboxylic acid (2-[$^{18}$F]-fluoro-ethyl)-amide (top: radioactivity channel, bottom: UV channel, 254 nm). The radiochemical purity was >99%.

Figure 2:
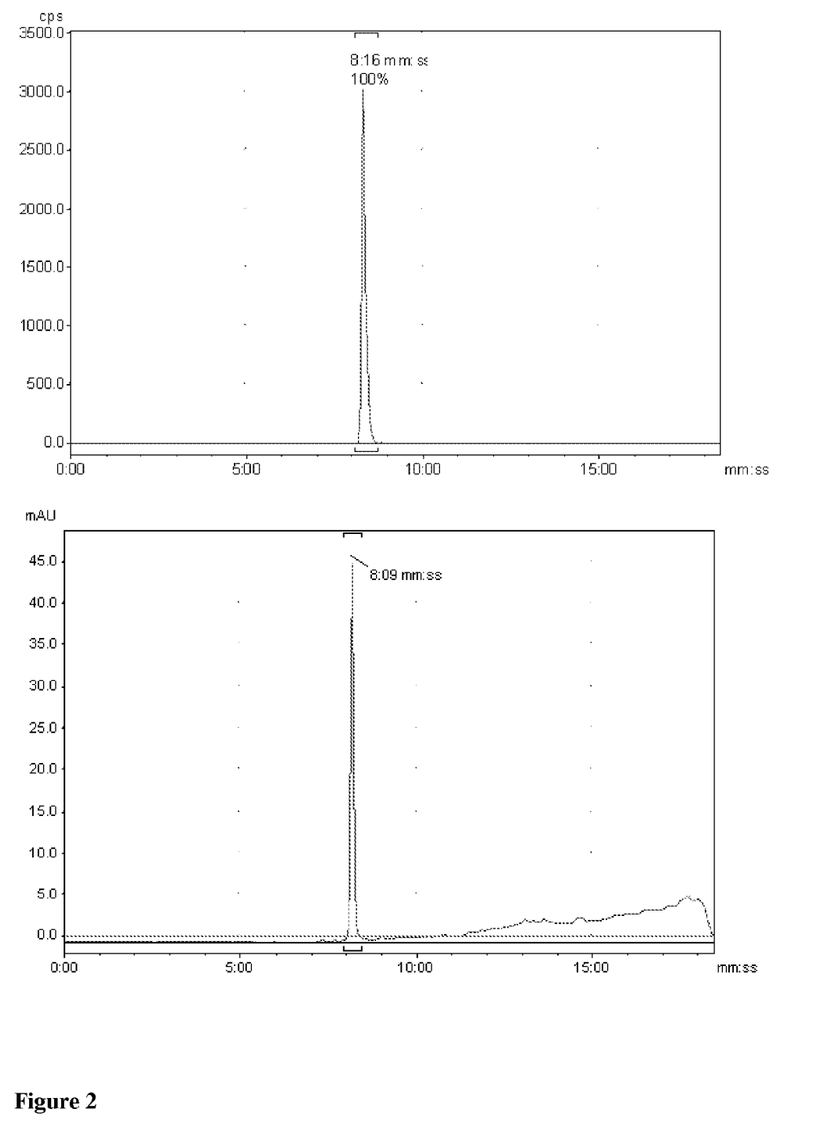
FIG. 2 shows the HPLC chromatogram for isolated and re-injected 9H-beta-Carboline-3-carboxylic acid (2-[$^{18}F$]fluoro-ethyl)-amide (top: radioactivity channel, bottom: UV channel, 254 nm).
Figure 3:
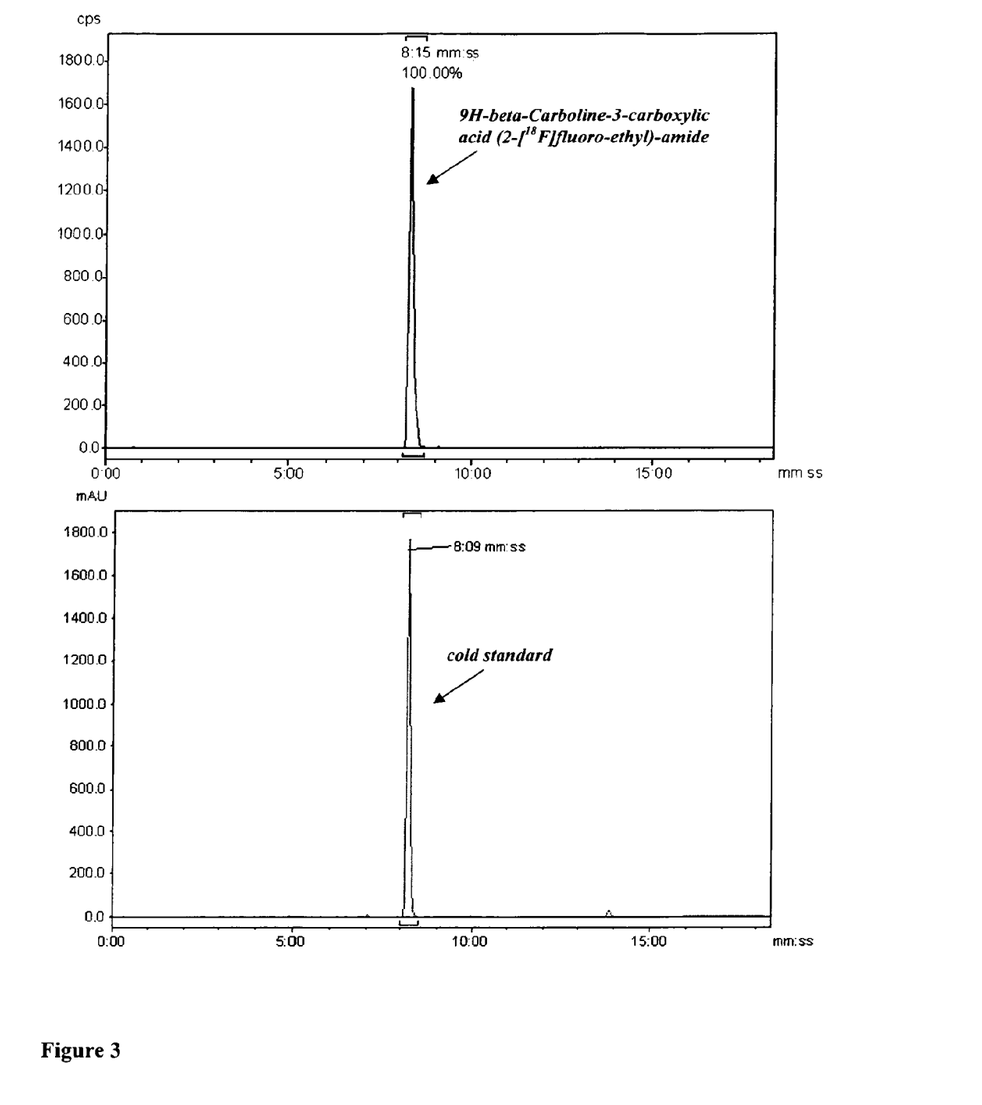
FIG. 3 shows the HPLC chromatogram for formulated 9H-beta-Carboline-3-carboxylic acid (2-[$^{18}F$]fluoro-ethyl)-amide with co-eluting standard compound (top: radioactivity channel, bottom: UV channel, 254 nm).

The collected HPLC product fraction was diluted with water (1 ml) and loaded onto a SepPak-C18 light cartridge that had been conditioned with ethanol (5 ml) and water (10 ml). The cartridge was flushed with water (5 ml). The product was eluted with ethanol in fractions of 0.1 ml. The formulated title compound was obtained in a total volume of 0.3 ml with 72 μCi (hottest fraction: 50 μCi in 0.1 ml). The formulation efficiency was 91%. FIG. 2 shows the HPLC chromatogram for isolated and re-injected 9H-beta-Carboline-3-carboxylic acid (2-[$^{18}$F]fluoro-ethyl)-amide (top: radioactivity channel, bottom: UV channel, 254 nm). FIG. 3 shows the HPLC chromatogram for formulated 9H-beta-Carboline-3-carboxylic acid (2-[$^{18}$F]fluoro-ethyl)-amide with co-eluting standard compound (top: radioactivity channel, bottom: UV channel, 254 nm).

Example 3

Figure 4:
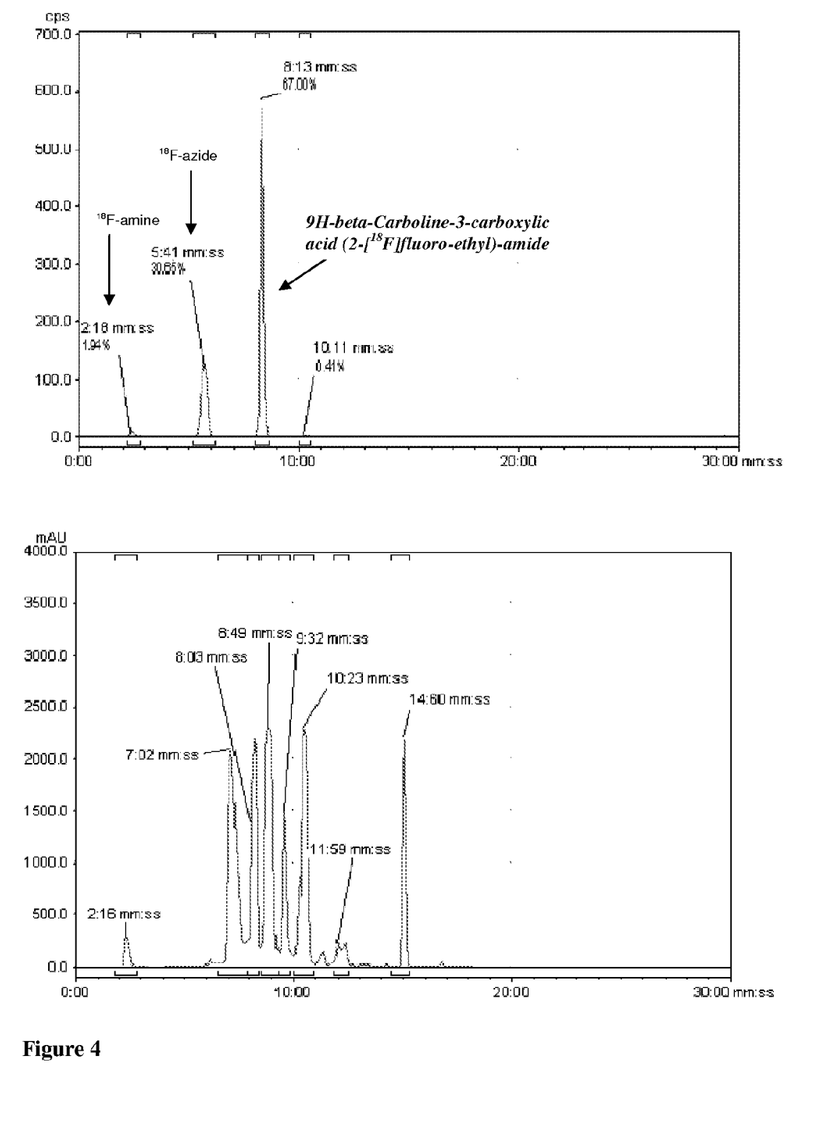
FIG. 4 shows the preparative HPLC chromatogram for 9H-beta-Carboline-3-carboxylic acid (2-[$^{18}F$]fluoro-ethyl)-amide using one-pot method (top: radioactivity channel, bottom: UV channel, 254 nm).

One-pot Preparation of 91'-beta-carboline-3-carboxylic acid (2-[$^{18}$F]fluoroethyl)amide A Wheaton vial (1 ml) was charged with a plug of copper wire (116 mg, Goodfellow, Cat. No. CU005240/1), aqueous methanesulfonic acid (100 μl, 14.8 mg, 0.154 mmol, 10% v/v), and 2-[$^{18}$F]-fluoroethylazide (12.4 mCi in 100 μl acetonitrile, prepared as described in M. Glaser and E. Årstad, Bioconj. Chem. 2007; 18: 989-993). After heating for 30 min at 80° C., triethylamine (90 μl, 0.770 mmol) was added. A solution of 9H-beta-Carboline-3-carboxylic acid pentafluorophenyl ester (4 mg, 10.6 mop in DMF (50 μl) was added. The mixture was incubated for 15 min at 80° C. and subsequently diluted with acetonitrile (100 μl). The reaction solution was filtered (PTFE Acrodisc, 0.45 μm) and injected onto the preparative HPLC. FIG. 4 shows the preparative HPLC chromatogram for 9H-beta-Carboline-3-carboxylic acid (2-[$^{18}$F]fluoro-ethyl)-amide using one-pot method (top: radioactivity channel, bottom: UV channel, 254 nm). The decay corrected radiochemical yield of the title compound with reference to 2-[$^{18}$F]-fluoroethylazide was 43% (3 mCi). The preparation time including formulation (described in Example 2) was 163 min.

Example 4

Synthesis of 2-[$^{18}$F]N-fluoroethyl benzamide

Figure 5A:
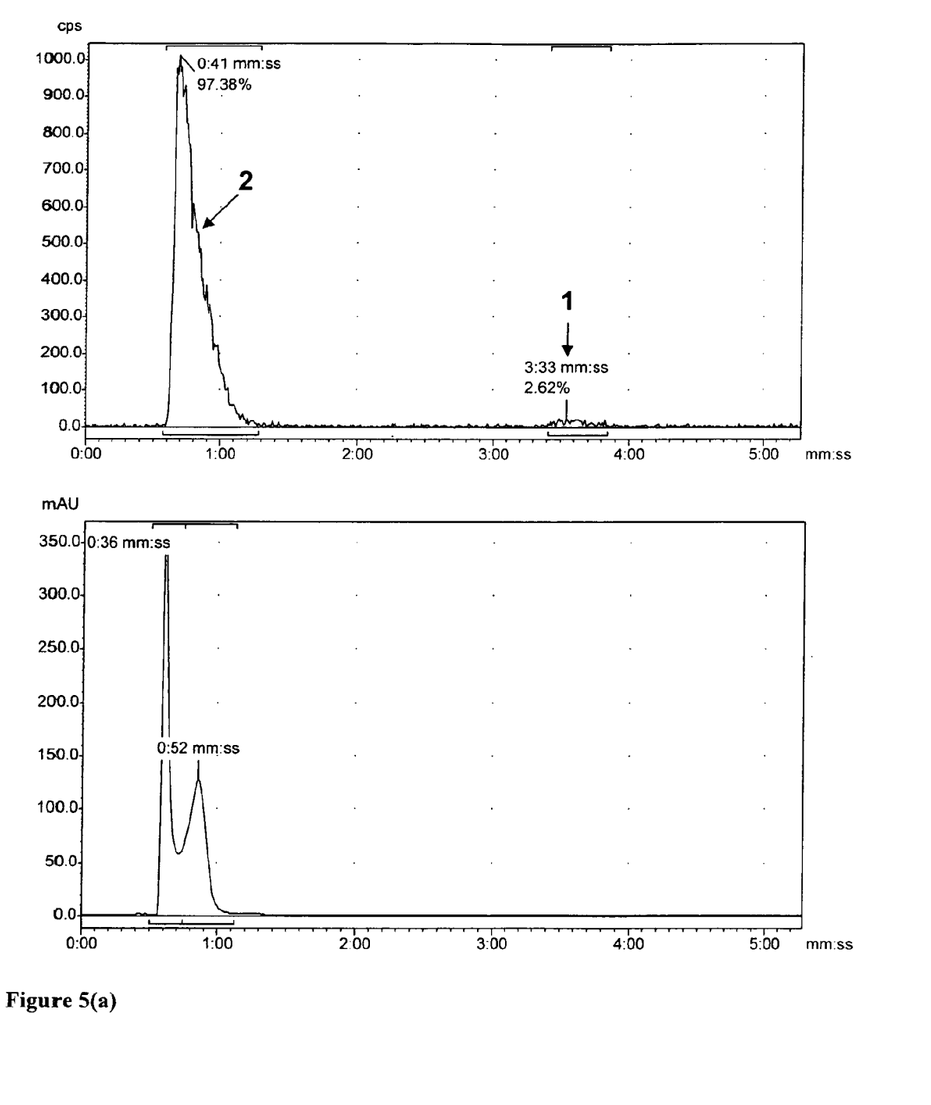
FIG. 5 shows the radio HPLC chromatograms: (a) after treating 1 in 5% TFA for 15 min at 60° C., (b) after reacting 2 with benzoyl chloride/triethylamine for 15 min at 60° C. showing the spiked reference for 3 at 7:09 min in the UV channel.
Figure 5B:
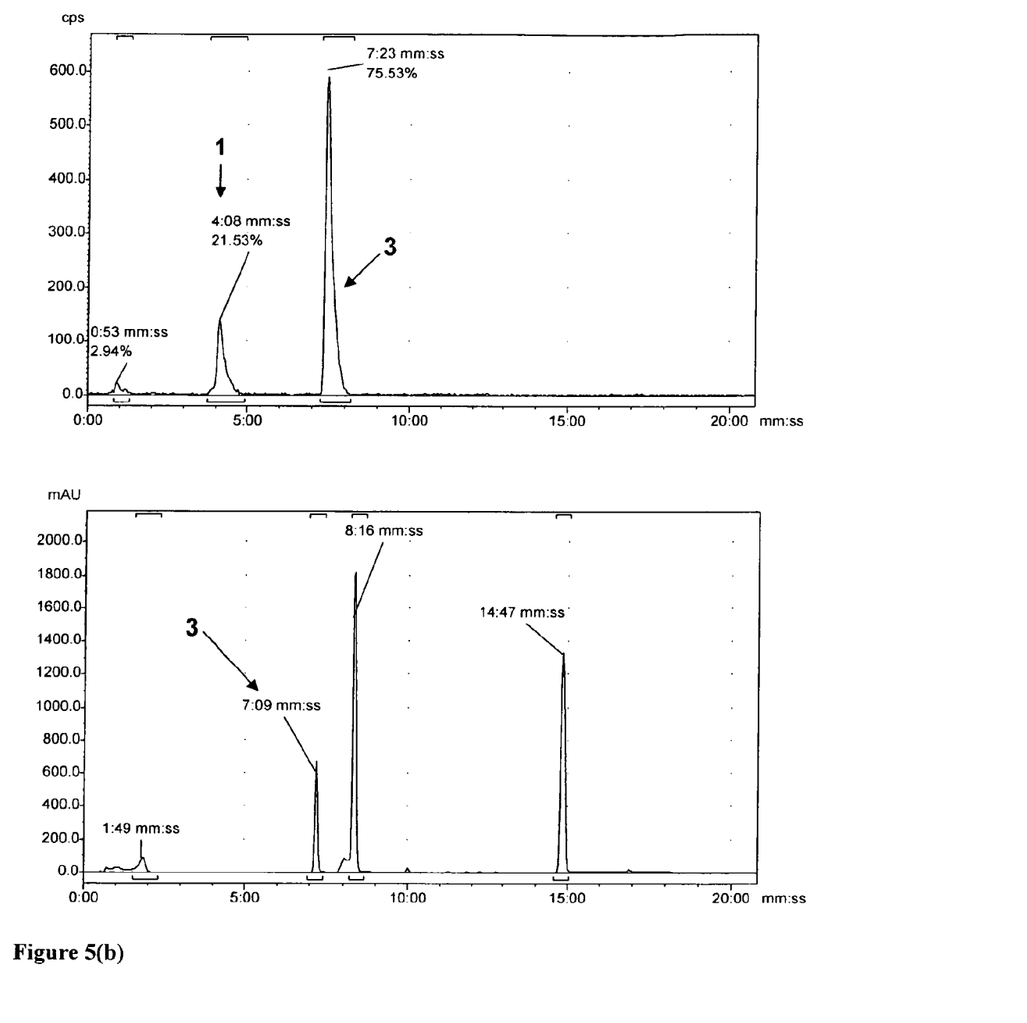

2-[$^{18}$F]fluoroethylazide (0.8 mCi in 50 μl acetonitrile, prepared as described in M. Glaser and E. Årstad, Bioconj. Chem. 2007; 18: 989-993) was mixed with water (50 μl) containing TFA (5 vol %) and copper powder (200 mg, 200 mesh). HPLC analysis after heating at 60° C. for 15 min showed a peak at the solvent front (2, 98%). To an aliquot of the reaction solution (50 μl) were added triethylamine (12 μl, 86 μmol) and benzoyl chloride (2.7 μl, 23 μmol). The mixture was analysed after heating 15 minutes at 60° C. for 15 min. The major product was 2-[$^{18}$F]N-fluoroethyl benzamide 3 (76%). The reaction product 3 was confirmed by co-elution with reference material. FIG. 5 shows the radio HPLC chromatograms: (a) after treating 1 in 5% TFA for 15 min at 60°

C., (b) after reacting 2 with benzoyl chloride/triethylamine for 15 min at 60° C. showing the spiked reference for 3 at 7:09 min in the UV channel.

Example 5

Preparation of Benzylamine from Benzylazide Using Copper Catalysis

A Wheaton vial was charged with benzylazide (21.2 mg, 160 μmol) dissolved in acetonitrile (200 μL). A solution of TFA in water (10% v/v, 200 μL) was added followed by copper powder (200 mg, –200 mesh). The mixture was stirred at 60° C. for 4.5 hours. After quenching with diethyl ether (1 mL) and hydrochloric acid (3 M, 1 mL) the organic layer was removed. The aqueous phase was washed with diethyl ether (1 mL) and neutralized with sodium hydroxide (3 M, 1 mL). The product was extracted with diethyl ether (1 mL) and washed with saturated sodium bicarbonate (0.5 mL) and saturated sodium thiosulfate (0.5 mL). The organic layer was separated and dried with brine (0.5 mL) and anhydrous sodium sulfate. The solvent was removed under a stream of nitrogen.

Yield: 9.4 mg (55%)

$^1$H NMR (300 MHz, CDCl$_3$) δ=3.88 (s, 2H), 7.32 (m, 5H).

What is claimed is:

1. A radiofluorination method comprising:
   (i) radiofluorination of an azide of Formula Ia with a suitable source of [$^{18}$F]-fluoride ion to obtain a radiofluorinated azide of Formula Ib:

wherein said radiofluorination is carried out in a solvent suitable for said radiofluorination, and wherein;

R$^1$ is C$_{1-10}$ alkylene, C$_{3-10}$ cycloalkylene, C$_{4-20}$ cycloalkylene-alkylene, C$_{5-14}$ arylene, C$_{6-20}$ alkylene-arylene, C$_{1-10}$ heteroalkylene, C$_{2-10}$ heterocycloalkylene, C$_{3-13}$ heteroarylene, C$_{6-20}$ heteroalkylene-arylene, C$_{6-20}$ alkylene-heteroarylene, or C$_{6-20}$ heteroalkylene-heteroarylene, wherein R$^1$ has between 0-3 substituents selected from C$_{1-4}$ alkyl, C$_{5-10}$ aryl, amino, hydroxy, halo or nitro; and, wherein R$^1$ optionally comprises one or more protecting groups;

and LG is a suitable leaving group;

(ii) reduction of the radiofluorinated azide of Formula Ib to obtain a radiofluorinated amine of Formula Ic:

$$H_2N-R^1-{}^{18}F \quad \text{(Ic)}$$

wherein said reduction is carried out in a solvent suitable for said reduction and catalysed by elemental copper in the presence of an acid; and wherein R$^1$ is as defined in step (i).

2. A radiofluorination method comprising:
   (i) radiofluorination of an azide of Formula Ia with a suitable source of [$^{18}$F]-fluoride ion to obtain a radiofluorinated azide of Formula Ib:

wherein said radiofluorination is carried out in a solvent suitable for said radiofluorination, and wherein;

R$^1$ is C$_{1-10}$ alkylene, C$_{3-10}$ cycloalkylene, C$_{4-20}$ cycloalkylene-alkylene, C$_{5-14}$ arylene, C$_{6-20}$ alkylene-arylene, C$_{1-10}$ heteroalkylene, C$_{2-10}$ heterocycloalkylene, C$_{3-13}$ heteroarylene, C$_{6-20}$ heteroalkylene-arylene, C$_{6-20}$ alkylene-heteroarylene, or C$_{6-20}$ heteroalkylene-heteroarylene, wherein R$^1$ has between 0-3 substituents selected from C$_{1-4}$ alkyl, C$_{5-10}$ aryl, amino, hydroxy, halo or nitro; and, wherein R$^1$ optionally comprises one or more protecting groups;

and LG is a suitable leaving group;

(ii) reduction of the radiofluorinated azide of Formula Ib to obtain a radiofluorinated amine of Formula Ic:

$$H_2N-R^1-{}^{18}F \quad \text{(Ic)}$$

wherein said reduction is carried out in a solvent suitable for said reduction and catalysed by elemental copper in the presence of an acid; and wherein R$^1$ is as defined in step (i);

(iii) reaction of the radiofluorinated amine of Formula Ic with a compound of Formula Id:

wherein:

R$^2$ is an R* group selected from C$_{1-10}$ alkyl, C$_{1-10}$ heteroalkyl, C$_{3-10}$ cycloalkyl, C$_{4-20}$ cycloalkyl-alkyl, C$_{5-14}$ aryl, C$_{3-13}$ heteroaryl, C$_{6-20}$ alkylene-aryl, C$_{6-20}$ heteroalkylene-aryl, C$_{6-20}$ alkylene-heteroaryl, C$_{6-20}$ heteroalkylene-heteroaryl, wherein R* is optionally substituted with one or more substituents selected from halo, amino, hydroxy, or nitro; or, R$^2$ is a biomolecule, or a nanoparticle; and, wherein R$^2$ optionally comprises one or more protecting groups; and,

R$^3$ is a suitable activating group (AG), to give a radiofluorinated amide of Formula IIa:

wherein R$^1$ is as defined in claim 1 and R$^2$ is as defined for Formula Id;

or;

R$^3$ is an R* group, to give a radiofluorinated amine of Formula IIb:

(IIb)

wherein $R^1$ is as defined in claim 1 and $R^2$ is as defined for Formula Id;
and wherein said reaction step (iii) is carried out in a solvent suitable for said reaction step.

3. The method as defined in claim 1 wherein $R^1$ is $C_{1-6}$ alkylene, $C_{1-6}$ heteroalkylene, $C_{3-10}$ cycloalkylene, $C_{5-14}$ arylene, or $C_{3-13}$ heteroarylene.

4. The method as defined in claim 1 wherein LG is selected from Cl, Br, I, tosylate (OTs), nosylate (ONs), brosylate (OBs), mesylate (OMs), and triflate (OTf).

5. The method as defined in claim 1 wherein said suitable source of [$^{18}$F]-fluoride ion of step (i) is a [$^{18}$F]-fluoride ion salt which comprises a cationic counterion selected from rubidium, caesium, potassium complexed with a cryptand, or tetraalkylammonium salts.

6. The method as defined in claim 2 wherein $R^2$ is an R* group.

7. The method as defined in claim 2 wherein R* is selected from $C_{1-10}$ alkyl, $C_{1-10}$ heteroalkyl, $C_{3-10}$ cycloalkyl, $C_{4-20}$ cycloalkyl-alkyl, $C_{5-14}$ aryl, $C_{3-13}$ heteroaryl, $C_{6-20}$ alkylene-aryl, $C_{6-20}$ heteroalkylene-aryl, $C_{6-20}$ alkylene-heteroaryl, $C_{6-20}$ heteroalkylene-heteroaryl.

8. The method as defined in claim 2 wherein the product is the amide of Formula IIa, and for step (iii) $R^3$ is AG.

9. The method as defined in claim 8 wherein said step (iii) is carried out in a dipolar aprotic solvent, in the presence of a base.

10. The method as defined in claim 8 wherein AG is selected from chloride, N-hydroxysuccinimidyl, N-hydroxyazobenzotriazolyl, pentafluorophenyl, and thiophenyl.

11. The method as defined in claim 2 wherein the product is the amine of Formula IIb, and for step (iii) $R^3$ is an R* group.

12. The method as defined in claim 11 wherein said step (iii) is carried out in a protic solvent.

13. The method as defined in claim 2 further including, in any order, one or more of the following steps:
(iv) when any of $R^{1-3}$ comprises one or more protecting groups, removal of said protecting groups; and/or,
(v) removal of excess [$^{18}$F]-fluoride ion, for example by ion-exchange chromatography; and/or,
(vi) where said solvent suitable for said reaction step (iii) is an organic solvent, removal of said solvent; and/or,
(vii) formulation of said radiofluorinated amide of Formula IIa or said radiofluorinated amine of Formula IIb together with a biocompatible carrier; and/or
(viii) sterilisation of the formulation of step (vii).

14. The method as defined in claim 1 which is carried out on an automated synthesis apparatus.

* * * * *